United States Patent [19]

Yamada et al.

[11] Patent Number: 4,555,487
[45] Date of Patent: Nov. 26, 1985

[54] METHOD FOR CULTIVATION OF PSEUDOMONAS BACTERIA

[75] Inventors: Hideaki Yamada, Kyoto; Koitchiro Ryuno, Yokohama, both of Japan

[73] Assignees: Nitto Kagaku Kogyo Kabushiki Kaisha, Tokyo; Hideaki Yamada, Kyoto, both of Japan

[21] Appl. No.: 551,852

[22] Filed: Nov. 15, 1983

[30] Foreign Application Priority Data

Oct. 13, 1983 [JP] Japan ................................ 58-191637

[51] Int. Cl.$^4$ .......................... C12N 1/20; C12N 9/78; C12P 13/02; C12R 1/38
[52] U.S. Cl. .................................... 435/253; 435/129; 435/227; 435/874
[58] Field of Search ........................ 435/253, 129, 227

[56] References Cited

U.S. PATENT DOCUMENTS 4,440,858  3/1984  Yamaguchi et al. ................ 435/129

OTHER PUBLICATIONS

Agricultural and Biological Chemistry, vol. 46, No. 5, pp. 1183–1189 (1982).

*Primary Examiner*—Lionel M. Shapiro
*Attorney, Agent, or Firm*—Robert E. Burns; Emmanuel J. Lobato; Bruce L. Adams

[57] ABSTRACT

Cells of Pseudomonas bacteria having a high nitrile hydratase activity can be obtained in a high yield by adding to a culture medium at least one amide compound selected from the group consisting of acrylamide, methacrylamide, crotonamide, and n-butyramide in the preparation of cells of bacteria having nitrile hydratase activity by cultivating Pseudomonas bacteria capable of producing nitrile hydratase.

3 Claims, No Drawings

METHOD FOR CULTIVATION OF PSEUDOMONAS BACTERIA

BACKGROUND OF THE INVENTION

The present invention relates to a method of producing in a high yield cells of Pseudomonas bacteria having a high nitrile hydratase activity.

In recent years, there have been increasing attempts to utilize microorganisms and enzymes as they are or in an immobilized state as catalysts for various single or complex chemical reactions.

Nitrile hydratase has been found by Hideaki Yamada, one of the present inventors, et al. as an enzyme capable of hydrating nitriles to produce the corresponding amides. (Reference: Agric. Biol. Chem. 46 1165 (1982)) As one example of the utilization of this enzyme, a method for preparation of acrylamide from acrylonitrile in the presence of bacteria having nitrile hydratase has been proposed. (References: Japanese Patent Laid-Open Pub. No. 86093/1983 (Japanese Patent Appln. No. 184688/1981) and Agric. Biol. Chem. 46 1183 (1982))

Under these circumstances, a method that can ensure the production of cells of Pseudomonas bacteria having a high nitrile hydratase activity in a high yield would be remarkably beneficial.

From the foregoing point of view, some of us have proposed a method in the concurrently filed U.S. patent application. The method for cultivation of Pseudomonas bacteria disclosed in this U.S. patent application comprises adding sequentially at least one compound selected from the group consisting of propionitrile, isobutyronitrile, propionamide, and isobutyramide to a culture medium in the preparation of cells of bacteria having nitrile hydratase activity by cultivating Pseudomonas bacteria capable of producing nitrile hydratase.

SUMMARY OF THE INVENTION

An object of the present invention is to solve the above problem by substantially the same means as is disclosed in the concurrently filed U.S. patent application mentioned previously on the basis of the discovery that specific amide compounds other than those named hereinbefore have similar advantages.

Thus, a distinguishing feature of the method for cultivation of Pseudomonas bacteria having a high nitrile hydratase activity according to this invention is the addition of at least one amide compound selected from the group consisting of acrylamide, methacrylamide, crotonamide, and n-butyramide to a culture medium in the preparation of cells of bacteria having nitrile hydratase activity by cultivating Pseudomonas bacteria capable of producing nitrile hydratase.

We have found that, by adding amide compounds to the culture medium during the cultivation of Pseudomonas bacteria, the nitrile hydratase activity per unit culture fluid increases remarkably.

This increase in nitrile hydratase activity per unit culture fluid is presumably traceable to the increase in cell concentration (i.e., yield) and cell activity (i.e., quantity of the nitrile hydratase in the cells).

In the present invention, amide compounds are sometimes called enzyme inducing agents in view especially of the latter factor although these compounds are effective not only in increasing the cell activity as has been set forth above.

DETAILED DESCRIPTION OF THE INVENTION

PSEUDOMONAS BACTERIA

The bacteria used in the present invention are Pseudomonas bacteria having nitrile hydratase activity and the capability of hydrating nitriles, particularly acrylonitrile, to produce the corresponding amides, particularly acrylamide. Specific examples of such bacteria are *Pseudomonas chlororaphis*, strain B 23 (FERM BP-187), and Pseudomonas sp., strain PS 1 (FERM BP-188), disclosed in Japanese Patent Laid-Open Pub. No. 86093/1983. The principal mycological properties of these bacteria are as follows.

|  |  | B 23 | PS 1 |
|---|---|---|---|
| (a) | Morphology | | |
| 1 | Shape and size of cell | bacillus 0.8–1.1 × 1.6–2.7 μm | bacillus 0.8–1.1 × 1.3–1.9 μm |
| 2 | Polymorphism | none | none |
| 3 | Motility | motile one to three polar flagella | motile with polar flagella |
| 4 | Formation of spores | none | none |
| 5 | Gram staining | — | — |
| 6 | Acid-fast property | — | — |
| (b) | Growth on various culture media | | |
| 1 | Bouillon-agar plate culture | spherical, convex, glossy, translucent and yellow | smooth, homogeneous, glossy, and mucoidal |
| 2 | Bouillon-agar slant culture | small colony formed | smooth, glossy, translucent, and yellow |
| 3 | Bouillon liquid culture | precipitated | |
| 4 | Bouillon-gelatin stab culture | liquified (+) | — |
| 5 | Litmus-milk | acidic: peptonized, not coagulated | alkaline: peptonized, not coagulated |
| (c) | Physiological properties | | |
| 1 | Reduction of nitrate | + | — |
| 2 | Denitrification | + | — |
| 3 | MR test | — | — |
| 4 | VP test | — | — |
| 5 | Formation of indole | — | — |
| 6 | Formation of hydrogen sulfide | — | — |
| 7 | Hydrolysis of starch | — | — |
| 8 | Utilization of citric acid | Simon's culture: + | Simon's culture: + |
| 9 | Utilization of inorganic nitrogen source | ammonium salt: + | ammonium salt: + |
| 10 | Formation of pigments | King-A culture: − King-B culture: + green (water-soluble) | King-A culture: − King-B culture: + green (water-soluble) |
| 11 | Urease | − | − |
| 12 | Oxidase | + | + |
| 13 | Catalase | + | + |
| 14 | Growth range | pH: 6.0–9.9 temperature: | |

-continued

| | B 23 | | PS 1 | |
|---|---|---|---|---|
| 15 Behavior toward oxygen | 5-36.5° C. aerobic | | aerobic | |
| 16 O-F Test | oxidized | | oxidized | |
| 17 Formation of acid & gas from saccharide | Formation of acid | Formation of gas | Formation of acid | Formation of gas |
| D-glucose | + | − | + | − |
| D-mannose | + | − | + | − |
| D-fructose | − | − | − | − |
| D-galactose | + | − | + | − |
| maltose | − | − | − | − |
| sucrose | − | − | − | − |
| lactose | − | − | − | − |
| trehalose | − | − | − | − |
| D-mannitol | − | − | − | − |
| glycerol | − | − | − | − |
| starch | − | − | − | − |
| 18 Nutritive requirements | none | | none | |
| 19 Other properties | See remarks | | | |
| Remarks: | Aminopeptidase | | + | |
| | Formation of levan from saccharose | | + | |
| | Formation of poly-β-hydroxybutyrate | | − | |
| | GC content | | 64.6% | |

ENZYME INDUCING AGENT

In the present invention, acrylamide, methacrylamide, crotonamide, or n-butyramide is used as an enzyme inducing agent. These compounds can be used singly or in the form of a mixture of two or more members.

In accordance with the present invention, these compounds are added to the culture medium at one time or sequentially. The term "sequentially" as used herein is intended to mean both "continuously" and "intermittently".

CULTIVATION - PRACTICE OF THE PRESENT INVENTION

A preferred embodiment of this invention will be described below.

Pseudomonas bacteria having nitrile hydratase activity are inoculated into a culture medium, especially an aqueous culture medium, containing carbon sources such as glucose, fructose, sucrose, dextrins, glycerol, ethanol, and succinic acid; nitrogen sources such as ammonia, ammonium sulfate, ammonium chloride, ammonium nitrate, and urea; organic nutriment sources such as yeast extract, a meat extract, malt extract, casein hydrolyzate, and peptone; inorganic salts such as phosphates; magnesium, potassium, and iron and other metals in trace amounts; and other substances. Cultivation is carried out under aerobic conditions while at least one species of the aforementioned amide compounds is added at one time or sequentially.

Ordinarily, the concentration of the enzyme inducing agent in the culture medium is adjusted preferably to lower than 50 g/l (in total when two or more compounds are used as such), and more preferably to 10 g/l or lower although this may vary depending on the cultivation time, temperature and other conditions. If the concentration becomes 50 g/l or higher, the nitrile hydratase activity of the bacteria will be lowered. The pH of the culture medium is of the order of 6 to 9, preferably of the order of 7 to 8, while the cultivation temperature is of the order of 20° to 37° C., preferably of the order of 25° to 30° C., and the cultivation time is about 1 to 3 days.

After the cultivation has been completed, the cells or nitrile hydratase can be collected or utilized in accordance with a procedure which will be described hereinlater in the experimental example.

In the disclosure, the letter "l" indicates "liter".

EXPERIMENTAL EXAMPLE

1. Cultivation of Bacteria 1.4 ml of a seed culture fluid obtained from *Pseudomonas chlororaphis*, strain B 23 (FERM BP-187), grown under the following precultivation conditions was cultivated under the subsequent cultivation conditions to determine the acrylamide-producing activity of the bacteria.

| (1) Precultivation Conditions | |
|---|---|
| MY culture medium (pH 7.6): | |
| peptone | 5 g/l |
| yeast extract | 3 g/l |
| malt extract | 3 g/l |
| glucose | 5 g/l |
| Cultivation temperature: 28° C. | |
| Cultivation time: 18 hours | |
| a 500-ml (net capacity: 50 ml) Sakaguchiflask was used. | |
| (2) Cultivation Conditions | |
| Culture medium (pH 7.6): | |
| sucrose | 10 g/l |
| $KH_2PO_4$ | 0.5 g/l |
| $K_2HPO_4$ | 0.5 g/l |
| $MgSO_4 .7H_2O$ | 0.5 g/l |
| $FeSO_4 .7H_2O$ | 20 mg/l |
| L-cystin | 2 g/l |
| L-glutamic acid | 2 g/l |
| L-proline | 2 g/l |
| amide compound(s) | 5 g/l |
| Cultivation temperature: 25° C. | |
| a 500-ml (net capacity 70 ml) Sakaguchiflask was used. | |

2. Measurement of Nitrile Hydratase Activity 1 ml of a culture fluid was admixed with 4 ml of a 1/10M phosphate buffer solution (pH 7.0), and 5 ml of a 1/10M phosphate buffer solution (pH 7.0) containing 5.0% by weight of acrylonitrile was added thereto. The resulting solution was caused to react at 10° C. for 10 minutes, and the bacterium cells therein were separated by filtration. The nitrile hydratase activity of the cells exhibited in the hydration of acrylonitrile to produce acrylamide was determined by measuring the quantity of the acrylamide (AA) thus obtained by means of gas chromatography.

The activity was determined for the specific activity (SA) and the total activity (TA) as defined below.

SA: μmole AA/mg-cells/min.
TA: μmole AA/ml-culture medium/min.

The results obtained are summarized in Table 1.

TABLE 1

| Amide compound* | Cultivation time(hr) | pH | Cell concentration (g/l) | Enzymatic activity | |
|---|---|---|---|---|---|
| | | | | SA | TA |
| AA | 30 | 7.00 | 2.15 | 5.14 | 11.05 |
| | 37 | 7.10 | 2.56 | 6.77 | 17.33 |
| | 44 | 7.55 | 2.38 | 2.21 | 5.26 |
| | 53 | 8.00 | 2.50 | 0 | 0 |
| CA | 19 | 6.90 | 4.05 | 28.88 | 117.0 |
| | 24 | 7.15 | 4.65 | 32.41 | 150.7 |
| | 30 | 7.68 | 3.93 | 29.92 | 117.6 |
| | 37 | 8.00 | 3.64 | 27.09 | 98.6 |

TABLE 1-continued

| Amide compound* | Cultivation time(hr) | pH | Cell concentration (g/l) | Enzymatic activity SA | Enzymatic activity TA |
|---|---|---|---|---|---|
| MA | 15 | 7.35 | 3.10 | 34.50 | 107.0 |
|  | 19 | 7.30 | 4.47 | 55.93 | 250.0 |
|  | 23 | 7.45 | 5.36 | 62.65 | 335.8 |
|  | 27 | 7.60 | 5.96 | 50.69 | 302.1 |
| BA | 15 | 7.10 | 5.30 | 7.64 | 40.5 |
|  | 19 | 7.00 | 7.45 | 5.81 | 43.3 |
|  | 23 | 7.18 | 8.46 | 4.93 | 41.7 |
|  | 27 | 7.25 | 8.40 | 4.71 | 39.6 |

*AA: acrylamide
CA: crotonamide
MA: methacrylamide
BA: n-butyramide

We claim:
1. A method for cultivation of Pseudomonas bacteria which comprises adding at least one amide compound selected from the group consisting of acrylamide, methacrylamide, crotonamide, and n-butyramide to a culture medium in the preparation of cells of bacteria having nitrile hydratase activity by cultivating Pseudomonas bacteria capable of producing nitrile hydratase.

2. A method as claimed in claim 1, wherein the concentration of the amide compound in the culture medium is lower than 50 g/l.

3. A method as claimed in claim 1, wherein the Pseudomonas bacteria capable of producing nitrile hydratase is *Pseudomonas chlororaphis*, strain B 23 (FERM BP-187), or Pseudomonas sp., strain PS 1 (FERM BP-188).

* * * * *